US010624580B2

(12) United States Patent
DeGroot et al.

(10) Patent No.: US 10,624,580 B2
(45) Date of Patent: Apr. 21, 2020

(54) VITAL SIGNS MONITORING SYSTEM

(71) Applicant: KONINKLIJKE PHILIPS N.V., Eindhoven (NL)

(72) Inventors: Koen Theo Johan DeGroot, Sevenum (NL); Alberto Giovanni Bonomi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 40 days.

(21) Appl. No.: 15/564,593

(22) PCT Filed: Apr. 8, 2016

(86) PCT No.: PCT/EP2016/057825
§ 371 (c)(1),
(2) Date: Oct. 5, 2017

(87) PCT Pub. No.: WO2016/162519
PCT Pub. Date: Oct. 13, 2016

(65) Prior Publication Data
US 2018/0078202 A1  Mar. 22, 2018

(30) Foreign Application Priority Data
Apr. 9, 2015  (EP) .................................... 15162997

(51) Int. Cl.
*A61B 5/00* (2006.01)
*A61B 5/024* (2006.01)
(Continued)

(52) U.S. Cl.
CPC .......... *A61B 5/4866* (2013.01); *A61B 5/0205* (2013.01); *A61B 5/02416* (2013.01);
(Continued)

(58) Field of Classification Search
CPC . A61B 5/4866; A61B 5/0205; A61B 5/02416; A61B 5/1118; A61B 5/681; A61B 2562/0219
(Continued)

(56) References Cited

U.S. PATENT DOCUMENTS

2004/0133081 A1*  7/2004  Teller ................... A61B 5/01
600/300
2007/0100666 A1*  5/2007  Stivoric .................. F24F 11/30
705/3

(Continued)

FOREIGN PATENT DOCUMENTS

EP    1424038 A1   6/2004
WO   2004073494 A2  9/2004
WO   2014207294 A1  12/2014

OTHER PUBLICATIONS

Search Report and Written Opinion of related application PCT/EP2016/057825, dated Jun. 9, 2016, 14 pages.
(Continued)

*Primary Examiner* — Carl H Layno
*Assistant Examiner* — Michael J Lau (57) ABSTRACT

A vital signs monitoring system comprises a processing unit (300) for estimating an activity energy expenditure (AEE), a first activity energy expenditure determining unit (320) for determining a first activity energy expenditure (AEEHR) based on heart rate data (HR), a second activity energy expenditure determining unit (330) for determining a second activity energy expenditure (AEEAC) based on motion data (AC), and a weighting unit (340) for determining a first and second weighting factor (wHR, wAC) based on a first and second probability relating to a high exertion (hH) and relating to a low exertion (hL), and activity energy expenditure calculating unit (350) for computing an overall activity energy expenditure (AEEO) based on the first activity (Continued)

energy expenditure (AEEHR) weighted by the first weighting factor (wHR) and on the second activity energy expenditure (AEEAC) weighted by the second weighting factor (wAC).

5 Claims, 6 Drawing Sheets (51) Int. Cl.
 *A61B 5/11* (2006.01)
 *A61B 5/0205* (2006.01)
(52) U.S. Cl.
 CPC ............ *A61B 5/1118* (2013.01); *A61B 5/681* (2013.01); *A61B 2562/0219* (2013.01)
(58) Field of Classification Search
 USPC ....................................................... 600/301
 See application file for complete search history.

(56) References Cited

U.S. PATENT DOCUMENTS

| | | | |
|---|---|---|---|
| 2008/0139952 A1 | 6/2008 | Kuroda et al. | |
| 2009/0177068 A1* | 7/2009 | Stivoric .................. | A61B 5/01 600/365 |
| 2011/0009713 A1* | 1/2011 | Feinberg .............. | A61B 5/0205 600/301 |
| 2011/0152635 A1* | 6/2011 | Morris ................... | G16H 10/20 600/301 |
| 2012/0083715 A1 | 4/2012 | Yuen et al. | |
| 2012/0245439 A1* | 9/2012 | Andre .................. | A61B 5/0205 600/310 |
| 2012/0310587 A1* | 12/2012 | Tu ............................ | G01D 1/16 702/141 |
| 2013/0116578 A1* | 5/2013 | An ........................ | A61B 5/0205 600/484 |
| 2013/0237778 A1* | 9/2013 | Rouquette .......... | A61B 5/02438 600/301 |
| 2014/0073486 A1* | 3/2014 | Ahmed .............. | A61B 5/02405 482/9 |
| 2014/0275838 A1* | 9/2014 | Osorio ................. | A61B 5/4094 600/301 |
| 2014/0335490 A1* | 11/2014 | Baarman ................ | A61B 5/002 434/236 |
| 2015/0057984 A1* | 2/2015 | Nicoletti ................ | G05B 15/02 703/2 |

OTHER PUBLICATIONS

Brage, et al., "Branched equation modeling of simultaneous accelerometry and heart rate monitoring improves estimate of directly measured physical activity energy expenditure", Journal of Applied Physiology, vol. 96, No. 1, Aug. 29, 2003, pp. 434-351.

* cited by examiner

VITAL SIGNS MONITORING SYSTEM

This application is the U.S. National Phase application under 35 U.S.C. § 371 of International Application No. PCT/EP2016/057825, filed on Apr. 8, 2016, which claims the benefit of European Application No. 15162997.9, filed Apr. 9, 2015. These applications are hereby incorporated by reference herein.

FIELD OF THE INVENTION

The invention relates to a vital signs monitoring system as well as to a method of monitoring vital signs or physiological parameters of a user.

BACKGROUND OF THE INVENTION

Heart rate sensors are well known to monitor or detect vital signs like a heart rate of a user. Such a heart rate sensor can be an optical heart rate sensor based on a photo-plethysmographic (PPG) sensor and can be used to acquire a volumetric organ measurement. By means of PPG sensors, changes in light absorption of a human skin is detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photodiode. The amount of light that is captured by the photo diode can be an indication of the blood volume inside the skin of a user. A PPG sensor can monitor the perfusion of blood in the dermis and subcutaneous tissue of the skin through an absorption measurement at a specific wavelength. If the blood volume is changed due to the pulsating heart, the scattered light coming back from the skin of the user is also changing. Therefore, by monitoring the detected light signal by means of the photodiode, a pulse of a user in his skin and thus the heart rate can be determined. Furthermore, compounds of the blood like oxygenated or de-oxygenated hemoglobin as well as oxygen saturation can be determined.

Figure 1:
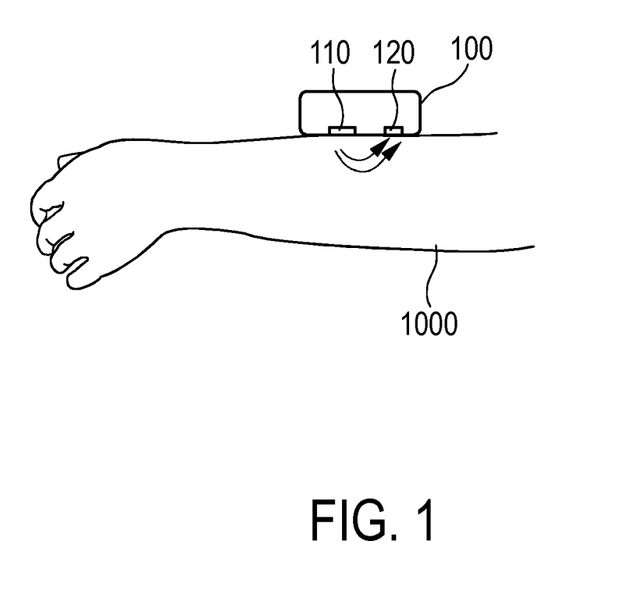
FIG. 1 shows a basic representation of an operational principle of a vital signs monitoring system.

FIG. 1 shows a basic representation of an operational principle of a heart rate sensor. In FIG. 1, a heart rate sensor 100 is arranged on an arm of a user. The heart rate sensor 100 comprises a light source 110 and a photo detector 120. The light source 110 emits light onto or in the skin 1000 of a user. Some of the light is reflected and the reflected light can be detected by the photo detector 120. Some light can be transmitted through tissue of the user and be detected by the photo detector 120. Based on the reflected or transmitted light, vital signs of a user like a heart rate can be determined.

The results of a heart rate sensor can be used to estimate or measure a caloric Activity Energy Expenditure AEE.

Figure 2:
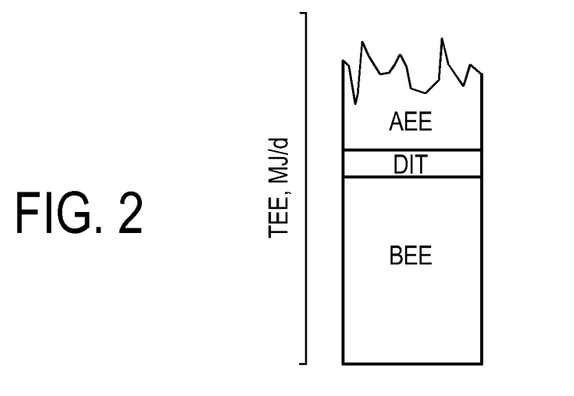
FIG. 2 shows a basic representation of a Total Energy Expenditure of a user.

FIG. 2 shows a representation of a total energy expenditure of a human being. The Total Energy Expenditure TEE is composed of a Basal Energy Expenditure BEE, a diet induced thermogenesis DIT and an Activity Energy Expenditure AEE. The Basal Energy Expenditure BEE is a combination of the sleeping metabolic rate and the energy expenditure from arousal.

If a user wants to for example reduce his weight, he must burn more calories than he is eating or drinking. The Activity Energy Expenditure AEE is that part of the Total Energy Expenditure TEE which is influenced by the activity of the person.

When a user is trying to reduce weight, it is often not easy for the user to determine how many calories he has spent throughout an activity or workout. Hence, there is a need for an accurate estimation or measurement of the energy spent during an activity.

An accurate estimation or measurement of the caloric Activity Energy Expenditure AEE is therefore an important factor for example for smart watches enabling sport and wellbeing applications.

Accordingly, it is desired to provide a monitor which can monitor the activity of a user during the day and which can measure or estimate the Activity Energy Expenditure, i.e. the energy expenditure of a user during a day.

Figure 3:
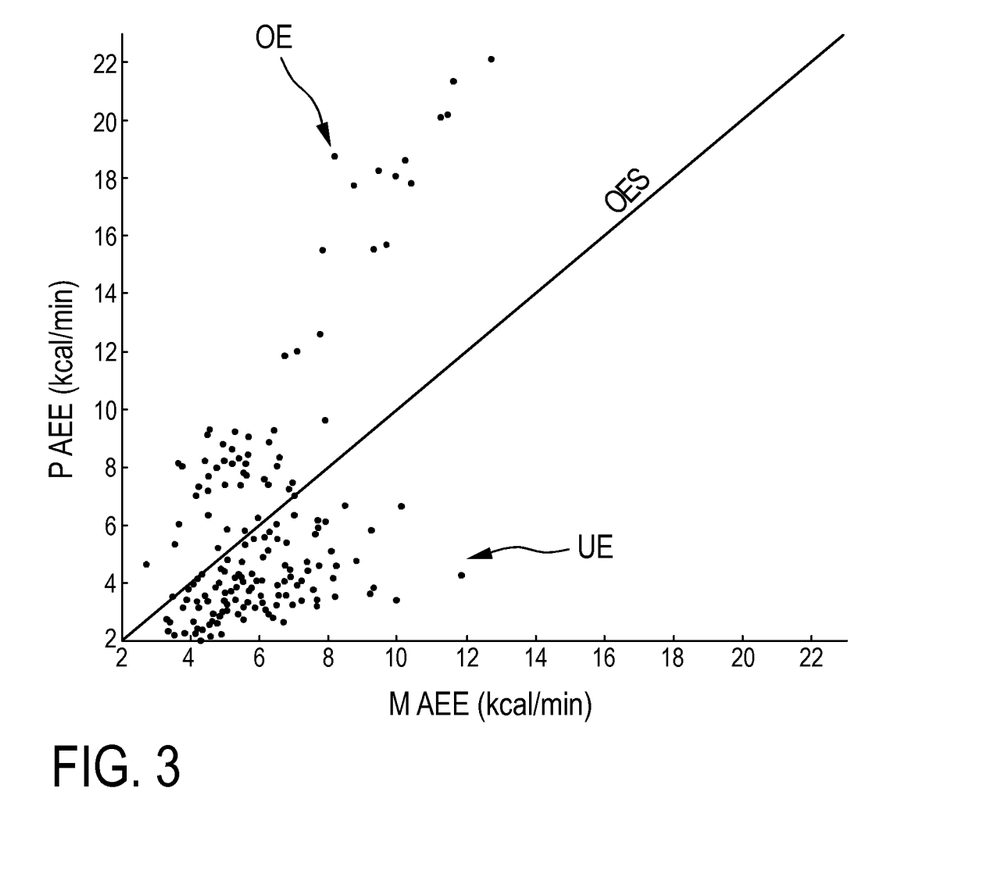
FIG. 3 shows a graph depicting an Activity Energy Expenditure prediction as a function of measured Activity Energy Expenditure.

FIG. 3 shows a graph indicating an Activity Energy Expenditure AEE prediction as a function of a measured Activity Energy Expenditure. In FIG. 3, the measured Activity Energy Expenditure MAEE is depicted at the X-axis and the predicted Activity Energy Expenditure PAEE is depicted at the Y-axis. Furthermore, in FIG. 3, several activity types like running, cycling, rowing, using a cross trainer etc. are depicted as data points. For some activities like walking, an overestimation OE (the estimated Activity Energy Expenditure AEE is too high) can be present. For other activities like cycling, rowing and using a cross trainer, an underestimation UE (the estimated Activity Energy Expenditure AEE is too low) can be present. In FIG. 3, furthermore, the optimal estimation OES is also depicted, namely the situation where the measured Activity Energy Expenditure MAEE corresponds to the predicted Activity Energy Expenditure.

The reasons why the measured and predicted Activity Energy Expenditure do not correspond to each other can be that the model based on which the predicted Activity Energy Expenditure AEE is determined is not accurate enough or the activity which the user is performing is not reflected good enough in the model.

According to FIG. 3, some activities requiring a high physical activity level may be misinterpreted or underestimated like cycling, rowing and using a cross trainer. In addition or alternatively to using heart rate data, the Activity Energy Expenditure AEE can be determined or estimated for example based on motion data of a user acquired from an acceleration sensor.

If a heart rate of a user is used to estimate the Activity Energy Expenditure AEE, it should be noted that the known linear relationship between the heart rate and the energy expenditure is only valid for aerobic activities with a moderate or vigorous exertion level. Furthermore, heart rate data which is measured for example during mental stress and fatigue may cause a biased prediction output in particular for low intensity activities. Furthermore, motion artifacts may be present in heart rate data. These motion artifacts may in particular occur during activities, which show an unpredictable thus non-repetitive movement pattern. Examples of such movements are several normal daily activities when full body motion is not represented by hand and wrist movement.

Furthermore, it should be noted that Activity Energy Expenditure AEE can be predicted quite accurately based on heart rate data during aerobic activities while acceleration and movement information are most suitable to predict Activity Energy Expenditure during sedentary, low intensity activities with a low exertion level or non-structured activities.

WO 2014/207294 A1 discloses a system for monitoring physical activity based on monitoring motion data of a user or alternatively based on a heart rate activity of a user.

EP 1 424 038 A1 discloses a device for measuring a calorie expenditure.

US 2008/0139952 A1 discloses a biometric information processing device which can display a calorie expenditure.

S. Brage. "Branched equation modeling of simultaneous accelerometry and heart rate monitoring improves estimate of directly measured physical activity energy expenditure", Journal of Applied Physiology, vol. 96, no. 1, 29 Aug. 2003, pages 343-351, discloses a vital signs monitoring system which computes an overall activity energy expenditure of a user. Static weight coefficients are determined offline during a training phase of a system. This is in particular performed by minimizing the root-mean-square error between a reference physical activity energy expenditure and an estimated activity energy expenditure derived from a mode with weight coefficients.

SUMMARY OF THE INVENTION

It is an object of the invention to provide a vital signs monitoring system which is able to accurately predict or measure an Activity Energy Expenditure of a user.

According to an aspect of the invention, a vital signs monitoring system is provided which comprises a processing unit configured to estimate an activity energy expenditure of a user. The processing unit comprises a first input configured to receive heart rate data HR from at least one heart rate sensor configured to measure or determine a heart rate HR of a user and a second input configured to receive motion or acceleration data AC from at least one motion sensor configured to detect motion or acceleration data AC of a user. The processing unit further comprises a first activity energy expenditure determining unit configured to determine a first activity energy expenditure based on heart rate data HR received via the first input. The processing unit further comprises a second activity energy expenditure determining unit configured to determine a second activity energy expenditure based on motion or acceleration data received via the second input. The processing unit furthermore comprises an estimation unit configured to estimate an exertion level of a user based on the current heart rate data from the at least one heart rate sensor and/or the current motion or acceleration data from the at least one motion sensor by estimating a first probability of a high exertion of a user and a second probability of a low exertion of a user. The processing unit further comprises a weighting unit configured to determine a first and second weighting factor based on a first probability relating to a high exertion level of the user and a second probability relating to a low exertion level of the user. The processing unit further comprises an activity energy expenditure calculating unit configured to compute overall activity energy expenditure based on the first activity energy expenditure weighted by the first weighting factor and on the second activity energy expenditure weighted by the second weighting factor.

According to an aspect of the invention the processing unit furthermore comprises a probability estimating unit configured for estimating a probability of a high or low exertion of a user. The weighting unit is then configured to determine the first and second weighting factor based on the probabilities of a high or low exertion level.

According to a further aspect of the invention an optical heart rate sensor in form of a photoplethysmographic sensor is configured to measure or determine a heart rate of a user. Moreover, at least one motion or acceleration sensor is configured to determine motion or acceleration data of a user.

According to a further aspect of the invention the processing unit, the at least one heart rate sensor and the at least one motion or acceleration sensor is arranged in a wearable device or a smart watch.

According to a further aspect of the invention a method of monitoring vital signs or physiological parameters of a user is provided. Heart rate data HR from at least one heart rate sensor configured to measure or determine a heart rate HR of a user is received. Motion or acceleration data from at least one motion sensor configured to detect motion or acceleration data of a user is received. A first activity energy expenditure based on heart rate data, and a second activity energy expenditure based on motion or acceleration data are determined. A first and second weighting factor based on a first probability relating to a high exertion level of a user and a second probability relating to a low exertion level of a user are determined. Overall activity energy expenditure is computed based on the first activity energy expenditure weight by the first weighting factor and on the second activity energy expenditure weighted by the second weighting factor.

It shall be understood that a preferred embodiment of the present invention can also be a combination of the dependent claims, above embodiments or aspects with respective independent claims.

These and other aspects of the invention will be apparent from and elucidated with reference to the embodiment(s) described hereinafter.

DETAILED DESCRIPTION OF EMBODIMENTS

Figure 4:
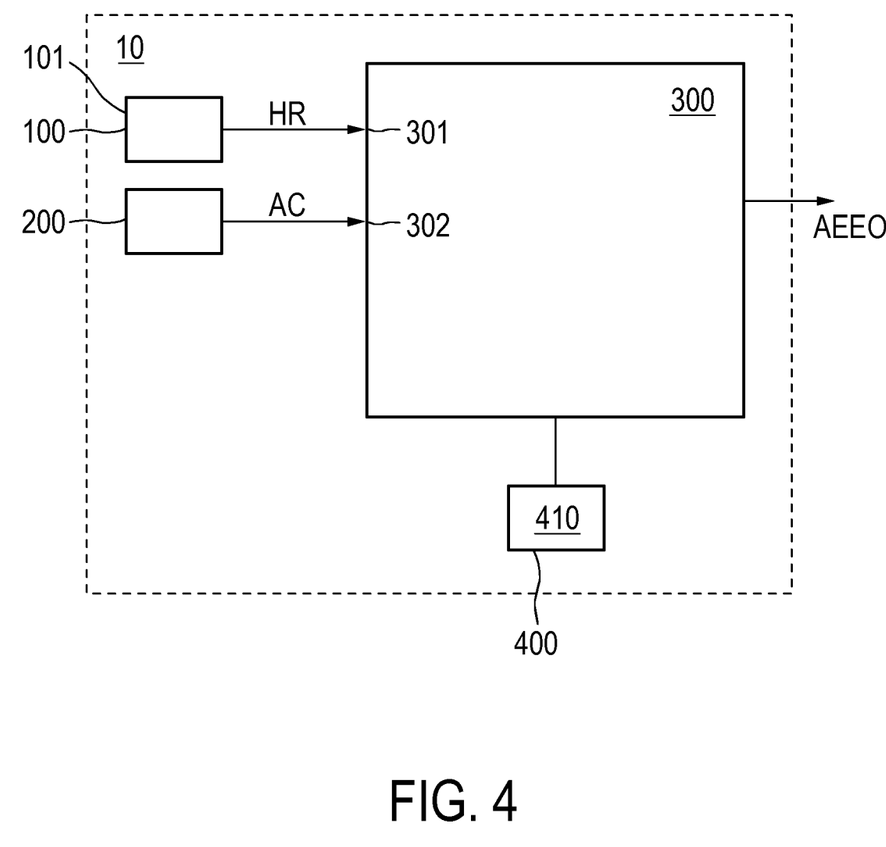
FIG. 4 shows a block diagram of a vital signs monitoring system according to an aspect of the invention.

FIG. 4 shows a block diagram of a vital signs monitoring system according to an aspect of the invention. The vital signs monitoring system is used to monitor vital signs or physiological parameters of a user. The vital signs monitor system 10 comprises at least one heart rate sensor 100, at least one motion sensor 200 for measuring or determining motion data or acceleration data AC of a user, a processing unit 300 such as a processor and optionally a display 400 with a graphic user interface 410. The processing unit 300 receives heart rate data HR from the at least one heart rate sensor 100 at its first input 301 and a motion or acceleration data AC from the at least one motion sensor 200 at its second input 302. The processing unit 300 is adapted to determine or estimate an Activity Energy Expenditure AEEO of a user based on the received heart rate data HR and/or the acceleration data AC. The heart rate sensor 100 can comprise a contact surface 101 which can be placed or arranged on a skin 1000 of a user to detect a heart rate of the user.

According to an aspect of the invention, an optical vital signs sensor is provided as a heart rate sensor 100 which is based on a photoplethysmographic PPG sensor. Such a PPG sensor is depicted in FIG. 1. A light source 110 emits light onto or into the skin 1000 of a user and some of the light is reflected and this reflected light can be detected by a photo detector 120. The output of the photo detector 120 can be analyzed to determine a heart rate or other vital signs of a user.

The output signal of the PPG sensor gives an indication on the blood movement in vessels of a user. The quality of the output signal of the PPG sensor can depend on the blood flow rate, skin morphology and skin temperature. In addition, optical losses in the PPG sensor may also have an influence on the quality of the output signal of the PPG sensor. The optical efficiency of the PPG sensor can depend on reflection losses when light penetrates from one media into another. Furthermore, a scattering of light at the surface of the skin of the user may also have an influence on the optical efficiency of the PPG sensor.

The PPG sensor or optical vital signs sensor according to an aspect of the invention can be implemented as a wearable device e.g. a wrist device (like a watch or smart watch). The optical vital signs sensor can also be implemented as a device worn behind the ear of a user, e.g. like a hearing aid. A wearable device is a device which can be worn or attached on a skin of a user.

The motion sensor 200 can also be implemented as a wearable device. Preferably, the motion sensor 120 and the heart rate sensor 110 are implemented in a common housing as part of a wearable device. The motion sensor 200 can be an acceleration sensor such as a piezoelectric, piezoresistive or a capacitive accelerometer.

Figure 5:
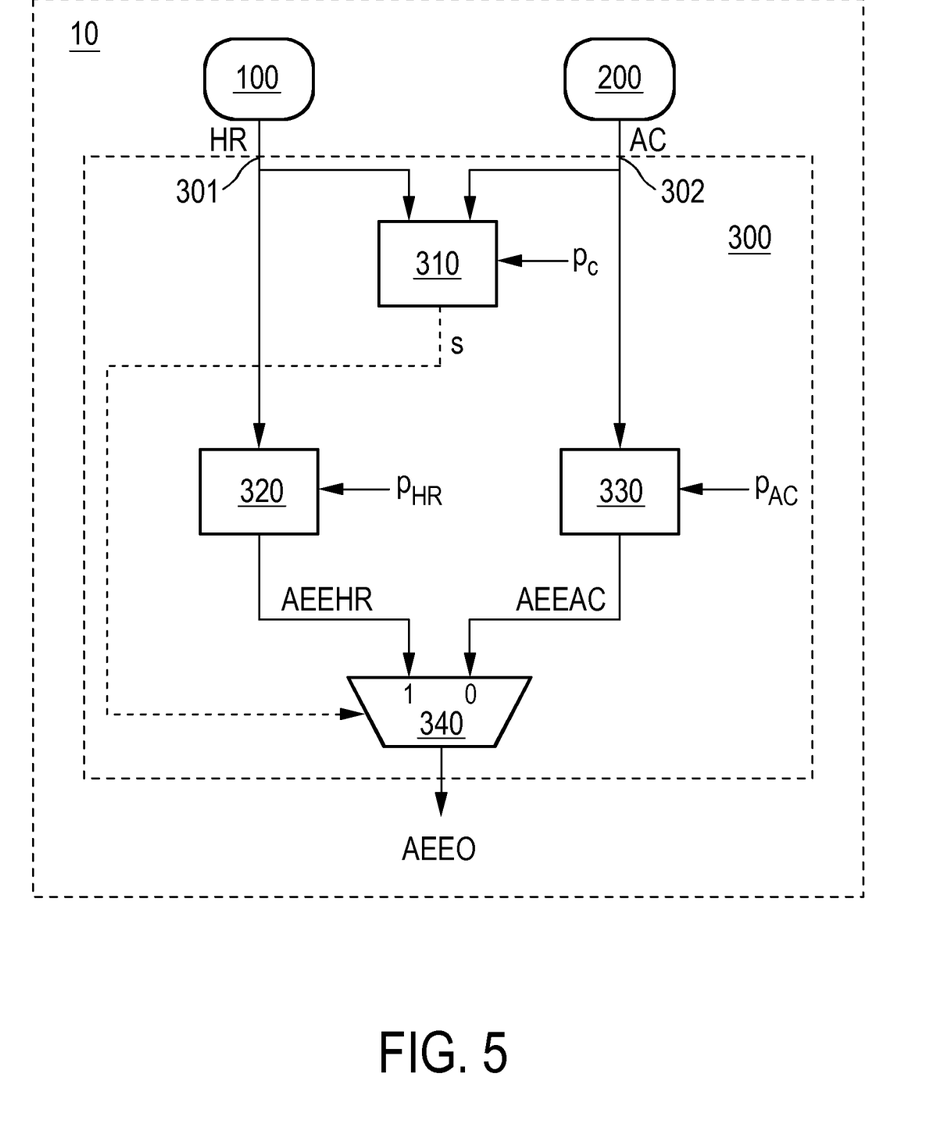
FIG. 5 shows a further block diagram of a vital signs monitoring system according to an aspect of the invention.

FIG. 5 shows a further block diagram of a vital signs monitoring system according to an aspect of the invention. The vital signs monitor system 10 comprises at least one heart rate sensor 100, at least one motion or acceleration sensor 200 and a processing unit 300. The processing unit 300 receives the heart rate data HR from the at least one heart rate sensor 100 at its first input 301 as well as a acceleration or motion data AC from the acceleration sensor 200 at its second input 302. The processing unit 300 outputs a predicted or estimated Activity Energy Expenditure AEEO.

The processing unit 300 can use the heart rate data HR from the at least one heart rate sensor 100 or the acceleration data AC from the acceleration sensor 200 to predict or determine an Activity Energy Expenditure AEE. In other words, the processing unit 300 can either use the heart rate data HR or the acceleration data AC. Alternatively, the processing unit 300 may also use a combination of the heart rate data HR and the acceleration data AC.

The processing unit 300 comprises an estimating unit 310 for estimating the exertion level of a person during a time interval. The estimating unit 310 receives the current heart rate data HR and the current acceleration data AC and analyzes these data. The estimation unit 310 outputs a signal s indicating whether the exertion level is high or low. The output signal S will correspond to "1" if the exertion level is estimated as high and will correspond to "0" if the exertion level is estimated as low. The estimating unit 310 has a further input for the parameter pc. This parameter pc can be used for controlling the sensitivity and specificity of the exertion level estimation performed by the estimation unit 310.

The processing unit 300 furthermore comprises a first Activity Energy Expenditure determining unit 320 which computes or estimates the Activity Energy Expenditure AEE based on the heart rate HR data from the at least one heart rate sensor 100. The first Activity Energy Expenditure determining unit 320 comprises a further input for a parameter set $P_{HR}$ which can be used to determine the sensitivity of the first determining unit 320. The first determining unit 320 outputs an Activity Energy Expenditure AEEHR for the activity expenditure based on the heart rate data HR.

The processing unit 300 furthermore comprises a second Activity Energy Expenditure determining unit 330 which computes or determines the Activity Energy Expenditure AEE based on the acceleration data AC from the at least one acceleration sensor or motion sensor 200. The second determining unit 330 comprises an input for a parameter set $P_{AC}$ for setting the sensitivity of the second determining unit 330. The second Activity Energy Expenditure determining unit 330 outputs an Activity Energy Expenditure AEEAC as determined based on the acceleration or motion data AC.

The processing unit 300 furthermore comprises a selecting unit 340 which selects the output of the first or second Activity Energy Expenditure determining unit 320, 330 based on the output signal s of the estimating unit 310. In particular, if the output signal s is high "1", then the output of the first Activity Energy Expenditure unit 320 is used while if the output signal is low "0", then the output of the second Activity Energy Expenditure determining unit 330 is used as output signal.

The vital signs monitoring system according to FIG. 5 has some drawbacks as a decision whether or not a high or low exertion level is present can sometimes not be accurately performed. Thus, in some cases, the decision whether or not the exertion level is high or low is prone to mistakes.

In addition, if the activity of a user is at the border between high and low exertion levels due to motion artifacts, the processing unit may switch between low and high exertion levels, thus changing the output of the processing unit and thereby the overall Activity Energy Expenditure during the physical activity such that the user may not receive an accurate and constant estimation of the activity level.

Figure 6:
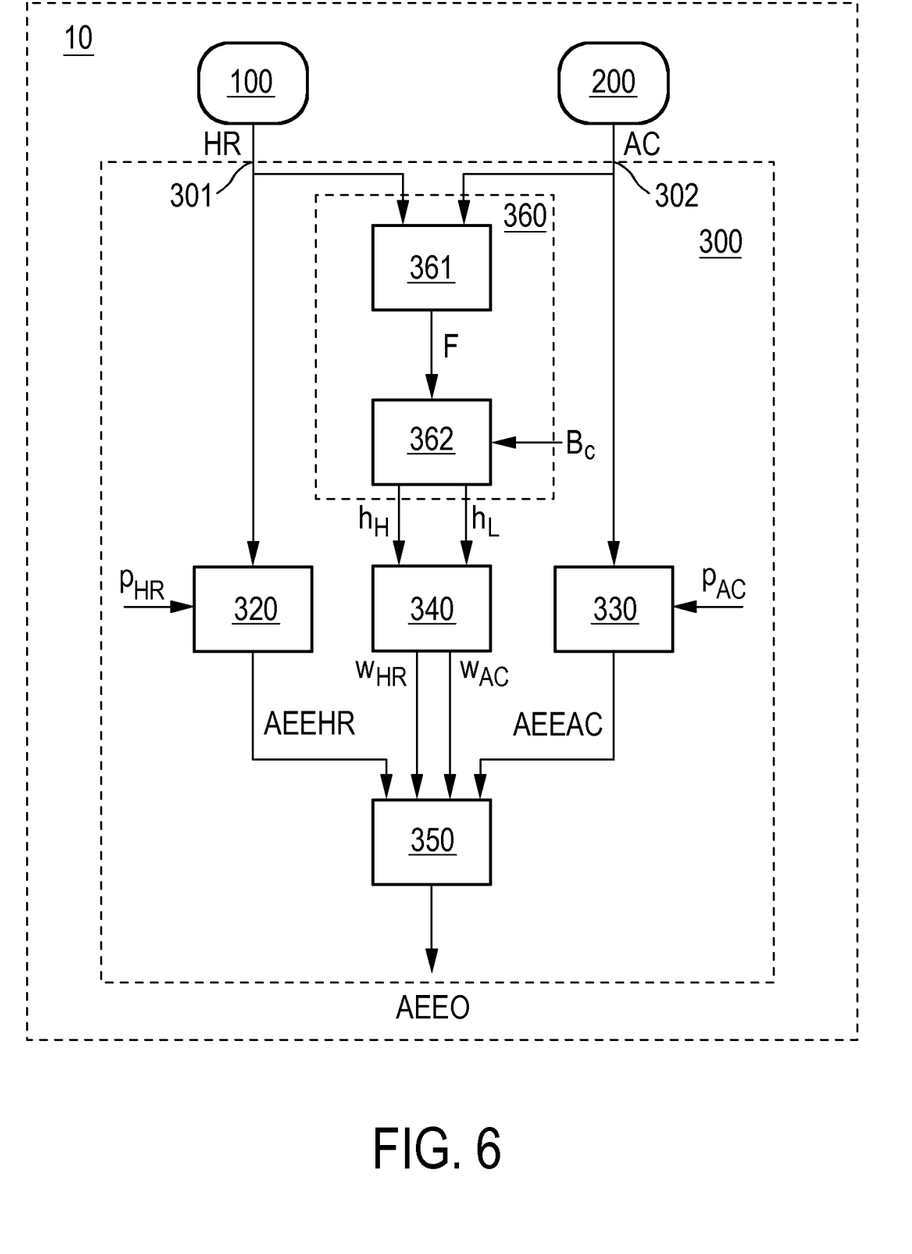
FIG. 6 shows a block diagram of a vital signs monitoring system according to a further aspect of the invention.

FIG. 6 shows a block diagram of a vital signs monitoring system according to a further aspect of the invention. The vital signs monitor system 10 comprises at least one heart rate sensor 100, at least one acceleration or motion sensor 200 and a processing unit 300. The heart rate sensor 100 outputs heart rate data HR and the acceleration or motion sensor 200 outputs acceleration or motion data AC. The processing unit 300 comprises a first Activity Energy Expenditure determining unit 320 for determining the Activity Energy Expenditure AEEHR based on the heart rate data HR from the at least one heart rate sensor 100. The processing unit furthermore comprises a second Activity Energy Expenditure determining unit 330 for determining the Activity Energy Expenditure AEEAC based on the motion data or acceleration data AC from the at least one acceleration sensor 200. The processing unit 300 furthermore comprises a probability unit 360 for determining a probability of a high or low exertion based on the heart rate data HR from the at least one heart rate sensor 100 as well as based on current acceleration or motion data AC from the at least one acceleration sensor 200. In other words, the probability unit 360 serves to estimate the probability of a high exertion or a low exertion level. The probability estimating unit 360 comprises a feature set unit 361 for extracting a feature set F based on the heart rate data HR, the motion data or acceleration data AC or a combination of both. The feature set F are used as predictors for a high or low body exertion. These predictors can be an activity count, speed, number of steps, motion level etc. The motion level can be used together with cardiac features from the heart rate data.

The feature set F can be inputted into a classification unit 362. The classification unit 362 is used to classify the exertion level of a person. The classification unit 362 can receive a parameter set Be. This parameter Be can optionally be derived during a training phase. The classification unit 362 outputs a probability of the high and low exertion as a function of the feature set F. A High exertion level correspond to aerobic activities, activities having a consistent and repetitive temporal pattern, which may represent planned actions of exertion level higher than resting low exertion level consists of activities involving irregular body movement, which result in predominant anaerobic work or low intensity sedentary occupations. The classification unit 362 may also use an estimated resting heart rate, an estimated maximum heart rate, the sex, age, height and weight of the user during the classification process. Optionally, the probabilities can be defined as $h_H(F)=P(y=1|F; B_c)$ and $h_L(F)=P(y=0|F; B_c)$.

The processing unit 300 furthermore comprises a weighting unit 340 for transforming the probability estimates $h_H$ and $h_L$ into weighting factors wHR and wAC. The weighting factors can be between 0 and 1.

The processing unit 300 furthermore comprises an Activity Energy Expenditure calculating unit 350, which is computing or determining the overall Activity Energy Expenditure AEEO. The overall Activity Energy Expenditure AEEO is defined as: $f_{WA}$ (wHR, wAC, AEEHR, AEEAC) such that the overall Activity Energy Expenditure AEEO=wHR·AEEHR+wAC·AEEAC. Accordingly, the overall Activity Energy Expenditure is based on a combination of the Activity Energy Expenditure determined based on the heart rate data HR as well as on the acceleration data AC with corresponding weighting factors.

According to a further aspect of the invention, instead of using two different parameters like heart rate HR and motion data AC for determining the Activity Energy Expenditure, the data of a plurality of sensors can be used to determine the Activity Energy Expenditure. The Activity Energy Expenditure AEE can be determined or estimated based on each of the N sensors such that each $i_{th}$ estimation unit produces an energy expenditure estimate. As in the aspect of the invention according to FIG. 6, weighting units are provided for analyzing the output signals of the sensor and optionally for incorporating supplementary subject specific information. The overall Activity Energy Expenditure AEE is then estimated by computing a weighted average of all separate energy expenditure estimates.

Figure 7:
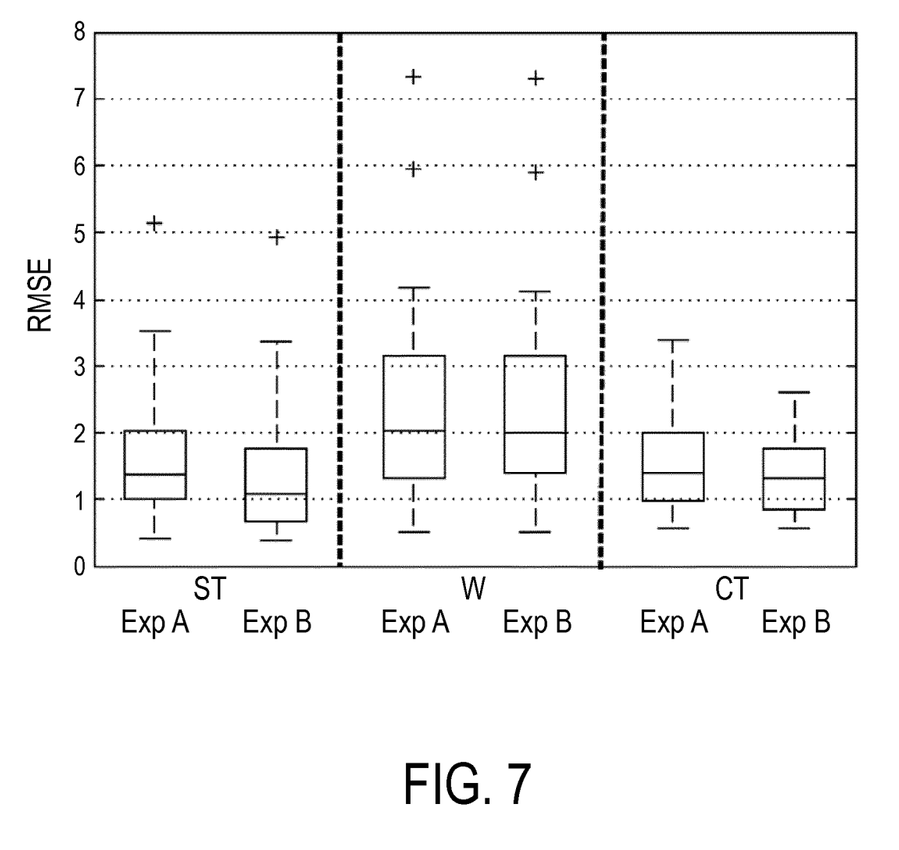
FIG. 7 shows a graph indicating an improved accuracy of a predicting Activity Energy Expenditure with a vital signs monitoring system according to an aspect of the invention.

FIG. 7 shows a graph indicating an improved accuracy of a predicting Activity Energy Expenditure AEE with a vital signs monitoring system according to an aspect of the invention. In FIG. 7, a comparison is depicted between the aspect of the invention according to FIG. 5 and according to FIG. 6. The results as achieved by the vital signs monitor system according to FIG. 5 are depicted as Exp A while the results achieved by the vital signs monitor system according to FIG. 6 are depicted as Exp B. In particular, three different tests have been performed, namely a step test ST, a walking at 3 km/h W and using a cross trainer CT has been used.

In table 1, examples of the weighting factors wHR and wAC are depicted.

| Activity type | wHR | wAC |
|---|---|---|
| Step Test ST | 0.79 | 0.21 |
| Walking 3 km/h W | 0.97 | 0.03 |
| Cross Trainer CT | 0.83 | 0.17 |

For the walking activity W, the weighting factors of the mixture of the Activity Energy Expenditure AEEHR based on the heart rate and the Activity Energy Expenditure AEEAC based on the acceleration data AC has no limiting effect as the weighting factor for the heart rate data is approximately 1, i.e. the overall Activity Energy Expenditure corresponds to the Activity Energy Expenditure based on the heart rate data. On the other hand, for the step test T and the cross trainer CT, the weighting factor $w_{HR}$ corresponds to 0.79 and 0.83, respectively while the weighting factor for the acceleration data corresponds to 0.21 and 0.17, respectively. Hence, the overall Activity Energy Expenditure can be calculated more accurately.

Table 2 shows the average RMSE as obtained from the two experiments described before.

| | Exp A (kcal/min) | Exp B (kcal/min) |
|---|---|---|
| Step Test ST | 1.67 | 1.47 |
| Walking 3 km/h W | 2.58 | 2.58 |
| Cross Trainer CT | 1.59 | 1.40 |

Accordingly, it can be seen that the average RMSE obtained from the second experiment has improved by 12% with respect to the first experiments. Regarding the walking exercise W, the RMSE substantially remains constant. Accordingly, the provision of the weighting factors is advantageous to estimate an exertion level.

In table 3, the standard deviations of the overall Activity Energy Expenditure AEE for the two experiments are disclosed.

| | Exp A (kcal/min) | Exp B (kcal/min) |
|---|---|---|
| Step Test ST | 1.05 | 0.88 |
| Walking 3 km/h W | 1.95 | 1.92 |
| Cross Trainer CT | 1.55 | 1.28 |

As can be seen from FIG. 3, by using the vital signs monitoring system according to FIG. 6, it is possible to reduce the variability in the overall Activity Energy Expenditure AEE. For the walking exercise W, the variation of the overall Activity Energy Expenditure remains substantially unchanged.

According to an aspect of the invention, a computer program product is provided which comprises: a computer readable memory storing computer program code means for causing the vital signs monitor system to carry out steps of the monitoring vital signs or physiological parameters of a user.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfill the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A vital signs monitoring system, comprising:
a processing unit configured to estimate an activity energy expenditure of a user, said processing unit comprises:
  a first input interface configured to receive heart rate data from at least one heart rate sensor configured to measure or determine a heart rate of a user,
  a second input interface configured to receive motion or acceleration data from at least one motion sensor configured to detect motion or acceleration data of a user,
  a first activity energy expenditure determining unit configured to determine a first activity energy expenditure based on heart rate data received via the first input interface,
  a second activity energy expenditure determining unit configured to determine a second activity energy expenditure based on motion or acceleration data received via the second input interface;
a probability estimating unit configured to calculate a first probability of a high exertion of a user and a second probability of a low exertion of the user wherein the probability estimating unit comprises:
  a feature set unit configured to extract a feature set F based on at least one of the heart rate data and/or the motion or acceleration data, wherein the feature set F serve as predictors of a high or low exertion,
  a classification unit configured to classify an exertion level and to output the first probability and the second probability as a function of the feature set F,
  a weighting unit configured to determine a first weighting factor and a second weighting factor based on the first and the second probability, respectively, and
  an activity energy expenditure calculating unit configured to compute an overall activity energy expenditure based on the first activity energy expenditure based on heart rate data weighted by the first weighting factor and on the second activity energy expenditure based on motion or acceleration data weighted by the second weighting factor;
wherein the first probability of a high exertion of the user ($h_H$) is calculated using the formula: $h_H(F)=P(y=1/F; B_c)$, and the second probability of a low exertion of the user ($h_L$) is calculated using the formula: $h_L(F)=P(y=0|F; B_c)$, where $B_c$ is a parameter set derived during a training phase for the use; and
a display to output the overall activity energy expenditure.

2. The vital signs monitoring system according to claim 1, further comprising a heart rate sensor in form of a photoplethysmographic sensor configured to measure or determine a heart rate of a user, and at least one motion or acceleration sensor configured to determine motion or acceleration data of a user.

3. A wearable device, comprising;
a display,
a heart rate sensor,
a motion sensor, and
a processing unit comprising:
  a first input interface configured to receive heart rate data from the heart rate sensor,
  a second input interface configured to receive motion or acceleration data from the motion sensor,
  a first activity energy expenditure determining unit configured to determine a first activity energy expenditure based on heart rate data received via the first input interface,
  a second activity energy expenditure determining unit configured to determine a second activity energy expenditure based on motion or acceleration data received via the second input interface,
  a probability unit configured to calculate a first probability of a high exertion of a user and a second probability of a low exertion of the user, wherein the probability unit comprises:
    a feature set unit configured to extract a feature set F based on at least one of the heart rate data and the motion or acceleration data, wherein the feature set F serves as predictors of a high or low exertion, and
    a classification unit configured to classify an exertion level and to output the first probability and the second probability as a function of the feature set F;
  a weighting unit configured to determine a first weighting factor and a second weighting factor based on the first probability and the second probability, and
  an activity energy expenditure calculating unit configured to compute an overall activity energy expenditure based on the first activity energy expenditure based on heart rate data weighted by the first weighting factor and on the second activity energy expenditure based on motion or acceleration data weighted by the second weighting factor;
wherein the first probability of a high exertion of the user ($h_H$) is calculated using the formula: $h_H(F)=P(y=1/F; B_c)$, and the second probability of a low exertion of the user ($h_L$) is calculated using the formula: $h_L(F)=P(y=0|F; B_c)$, where $B_c$ is a parameter set derived during a training phase for the user, and wherein the overall activity expenditure is displayed on the display.

4. A method of monitoring vital signs or physiological parameters of a user, comprising the steps of:
receiving heart rate data from at least one heart rate sensor configured to measure or determine a heart rate of a user;
receiving motion or acceleration data from at least one motion sensor configured to detect motion or acceleration data of a user;
determining a first activity energy expenditure based on the received heart rate data;
determining a second activity energy expenditure based on the received motion or acceleration data;
calculating a first probability of a high exertion of a user and a second probability of a low exertion of the user;

extracting a feature set F based on at least one of the heart rate data and the motion or acceleration data, wherein the feature set F serve as predictors of a high or low exertion;

classifying an exertion level and outputting the first and second probability as a function of the feature set F;

determining a first and second weighting factor based on the first probability and the second probability;

computing an overall activity expenditure based on the first activity energy expenditure based on heart rate data weighted by the first weighting factor and on the second activity energy expenditure based on motion or acceleration data weighted by the second weighting factor; and displaying the overall activity expenditure on a display;

wherein the first probability of a high exertion of the user ($h_H$) is calculated using the formula: $h_H(F)=P(y=1|F; B_c)$, and the second probability of a low exertion of the user ($h_L$) is calculated using the formula: $h_L(F)=P(y=0|F; B_c)$, where $B_c$ is a parameter set derived during a training phase for the user.

5. A non-transitory computer program product comprising computer program code instructions that, when executed, perform the steps of:

receiving heart rate data from at least one heart rate sensor configured to measure or determine a heart rate of a user;

receiving motion or acceleration data from at least one motion sensor configured to detect motion or acceleration data of a user;

determining a first activity energy expenditure based on the received heart rate data;

determining a second activity energy expenditure based on the received motion or acceleration data;

calculating a first probability of a high exertion of a user and a second probability of a low exertion of the user;

extracting a feature set F based on at least one of the heart rate data and the motion or acceleration data, wherein the feature set F serve as predictors of a high or low exertion;

classifying an exertion level and outputting the first and second probability as a function of the feature set F;

determining a first and second weighting factor based on the first probability and the second probability;

computing an overall activity energy expenditure based on the first activity energy expenditure based on heart rate data weighted by the first weighting factor and on the second activity energy expenditure based on motion or acceleration data weighted by the second weighting factor; and displaying the overall activity energy expenditure on a display;

wherein the first probability of a high exertion of the user ($h_H$) is calculated using the formula: $h_H(F)=P(y=1|F; B_c)$, and the second probability of a low exertion of the user ($h_L$) is calculated using the formula: $h_L(F)=P(y=0|F; B_c)$, where $B_c$ is a parameter set derived during a training phase for the user.

\* \* \* \* \*